(12) United States Patent
Pastore et al.

(10) Patent No.: US 6,965,797 B2
(45) Date of Patent: Nov. 15, 2005

(54) METHOD AND APPARATUS FOR ASSESSING AND TREATING MYOCARDIAL WALL STRESS

(75) Inventors: Joseph M. Pastore, Minneapolis, MN (US); Steven D. Girouard, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 340 days.

(21) Appl. No.: 10/244,089

(22) Filed: Sep. 13, 2002

(65) Prior Publication Data

US 2004/0054381 A1 Mar. 18, 2004

(51) Int. Cl.[7] .............................................. A61N 1/362
(52) U.S. Cl. ......................................... 607/17; 607/25
(58) Field of Search ............................... 607/9, 17–19, 607/25, 44, 50, 21

(56) References Cited

U.S. PATENT DOCUMENTS

| | | | |
|---|---|---|---|
| 4,354,497 A | 10/1982 | Kahn ...................... 128/419 D |
| 4,549,548 A | 10/1985 | Wittkampf et al. .... 128/419 PG |
| 4,554,922 A | 11/1985 | Prystowsky et al. ........ 128/419 |
| 4,628,934 A | 12/1986 | Pohndorf et al. |
| 4,674,518 A | 6/1987 | Salo ........................... 128/695 |
| 4,686,987 A | 8/1987 | Salo et al. ............. 128/419 PG |
| 4,872,459 A | 10/1989 | Pless et al. ........... 128/419 PG |
| 4,880,005 A | 11/1989 | Pless et al. ........... 128/419 PG |
| 4,928,688 A | 5/1990 | Mower .................. 128/419 PG |
| 5,014,698 A | 5/1991 | Cohen ........................ 128/419 |
| 5,058,605 A | 10/1991 | Slovak |
| 5,109,842 A | 5/1992 | Adinolfi ......................... 607/2 |
| 5,137,019 A | 8/1992 | Pederson et al. ........... 128/419 |
| 5,156,149 A | 10/1992 | Hudrlik ................. 128/419 PG |
| 5,158,079 A | 10/1992 | Adams et al. .......... 128/419 D |
| 5,174,289 A | 12/1992 | Cohen ................... 128/419 PG |
| 5,190,035 A | 3/1993 | Salo et al. ................... 128/419 |
| 5,233,985 A | 8/1993 | Hudrlik ........................ 607/27 |
| 5,267,560 A | 12/1993 | Cohen .......................... 607/25 |
| 5,284,136 A | 2/1994 | Hauck et al. ................. 607/24 |
| 5,334,222 A | 8/1994 | Salo et al. .................... 607/17 |
| 5,370,665 A | 12/1994 | Hudrlik ......................... 607/9 |
| 5,391,190 A | 2/1995 | Pederson et al. ............. 607/23 |
| 5,417,717 A | 5/1995 | Salo et al. .................... 607/18 |
| 5,487,752 A | 1/1996 | Salo et al. .................... 607/17 |
| 5,514,161 A | 5/1996 | Limousin ....................... 607/9 |
| 5,534,016 A | 7/1996 | Boute ............................ 607/9 |

(Continued)

FOREIGN PATENT DOCUMENTS

EP 0522693 1/1993 ............ A61N 1/39

(Continued)

OTHER PUBLICATIONS

Arnaud, Claire, et al., "iNOS is a mediator of the heat stress-induced preconditioning against myocardial infarction in vivo in the rat", *Cardiovascular Research*, 58, (2003),118-125.

(Continued)

Primary Examiner—Carl Layno
(74) Attorney, Agent, or Firm—Schwegman, Lundberg, Woessner & Kluth, P.A.

(57) ABSTRACT

An apparatus and method for assessing myocardial wall stress is disclosed. The method may be used in conjunction with electro-stimulatory therapy for preventing or reversing ventricular remodeling. In such therapy, one or more stimulatory pulses are delivered to the heart such that a stressed region of the myocardium is pre-excited relative to other regions, thereby subjecting the stressed region to a lessened preload and afterload during systole. The unloading of the stressed myocardium over time effects reversal of undesirable ventricular remodeling.

22 Claims, 3 Drawing Sheets

U.S. PATENT DOCUMENTS

| | | | |
|---|---|---|---|
| 5,584,867 A | 12/1996 | Limousin et al. | 607/9 |
| 5,584,868 A | 12/1996 | Salo et al. | 607/17 |
| 5,674,259 A | 10/1997 | Gray | 607/20 |
| 5,683,429 A | 11/1997 | Mehra | 607/14 |
| 5,792,203 A | 8/1998 | Schroeppel | 607/30 |
| 5,797,970 A | 8/1998 | Pouvreau | 607/9 |
| 5,824,019 A | 10/1998 | Rueter et al. | 607/17 |
| 5,836,974 A | 11/1998 | Christini et al. | 607/5 |
| 5,851,226 A | 12/1998 | Skubitz et al. | 607/126 |
| 5,935,160 A | 8/1999 | Auricchio et al. | 607/122 |
| 5,995,871 A | 11/1999 | Knisley | |
| 6,022,322 A | 2/2000 | Prutchi | 600/506 |
| 6,038,483 A | 3/2000 | KenKnight et al. | 607/127 |
| 6,058,328 A | 5/2000 | Levine et al. | 607/14 |
| 6,058,329 A | 5/2000 | Salo et al. | 607/17 |
| 6,066,094 A * | 5/2000 | Ben-Haim | 600/437 |
| 6,112,117 A | 8/2000 | KenKnight et al. | 607/5 |
| 6,151,524 A | 11/2000 | Krig et al. | 607/14 |
| 6,152,955 A | 11/2000 | KenKnight et al. | 607/129 |
| 6,161,042 A | 12/2000 | Hartley et al. | 607/20 |
| 6,223,082 B1 | 4/2001 | Bakels et al. | 607/17 |
| 6,253,107 B1 | 6/2001 | Albrecht et al. | 607/9 |
| 6,272,377 B1 | 8/2001 | Sweeney et al. | 600/515 |
| 6,273,377 B1 | 8/2001 | Archer | 600/515 |
| 6,278,894 B1 | 8/2001 | Salo et al. | 600/547 |
| 6,285,898 B1 | 9/2001 | Ben-Haim | 600/374 |
| 6,292,694 B1 | 9/2001 | Schloss et al. | 607/9 |
| 6,361,522 B1 | 3/2002 | Scheiner et al. | 604/67 |
| 6,363,279 B1 | 3/2002 | Ben-Haim et al. | 607/9 |
| 6,370,424 B1 | 4/2002 | Prutchi | 600/547 |
| 6,418,343 B1 | 7/2002 | Zhang et al. | 607/9 |
| 6,427,084 B2 | 7/2002 | Baker et al. | 607/9 |
| 6,453,191 B2 | 9/2002 | Krishnamachari | 600/515 |
| 6,542,775 B2 | 4/2003 | Ding et al. | 607/24 |
| 6,574,506 B2 | 6/2003 | Kramer et al. | 607/9 |
| 6,628,988 B2 * | 9/2003 | Kramer et al. | 607/9 |
| 6,640,135 B1 | 10/2003 | Salo et al. | 607/9 |
| 6,684,103 B2 | 1/2004 | Ding et al. | 607/23 |
| 2002/0002389 A1 | 1/2002 | Bradley et al. | 607/8 |
| 2002/0115081 A1 | 8/2002 | Lee et al. | 435/6 |
| 2003/0023278 A1 * | 1/2003 | Pastore et al. | 607/9 |
| 2003/0055461 A1 | 3/2003 | Girouard et al. | 607/17 |
| 2003/0105493 A1 * | 6/2003 | Salo | 607/9 |
| 2003/0153952 A1 | 8/2003 | Auricchio et al. | 607/9 |
| 2003/0171791 A1 | 9/2003 | KenKnight et al. | 607/60 |
| 2003/0187482 A1 | 10/2003 | Pastore et al. | 607/9 |
| 2003/0208240 A1 | 11/2003 | Pastore et al. | 607/17 |
| 2003/0233132 A1 | 12/2003 | Pastore et al. | 607/17 |
| 2004/0030357 A1 | 2/2004 | Salo et al. | 607/17 |
| 2004/0044374 A1 * | 3/2004 | Weinberg et al. | 607/25 |
| 2004/0049236 A1 | 3/2004 | Kramer et al. | 607/9 |
| 2004/0073093 A1 | 4/2004 | Hatlestad | 600/300 |
| 2004/0098057 A1 | 5/2004 | Pastore | 607/11 |
| 2004/0127792 A1 | 7/2004 | Siejko et al. | 600/439 |
| 2005/0065568 A1 * | 3/2005 | Liu et al. | 607/17 |

FOREIGN PATENT DOCUMENTS

| | | | | |
|---|---|---|---|---|
| WO | WO-97/25098 | 7/1997 | | A61N 1/00 |
| WO | WO-99/10042 | 3/1999 | | A61N 1/362 |
| WO | WO-00/04947 | 2/2000 | | A61N 1/362 |
| WO | WO-00/09206 | 2/2000 | | A61N 1/362 |
| WO | WO-01/08748 | 2/2001 | | A61N 1/362 |
| WO | WO-01/30436 | 5/2001 | | |
| WO | WO-01/76689 | 10/2001 | | A61N 1/00 |
| WO | WO-02/087694 | 11/2002 | | A61N 1/368 |

OTHER PUBLICATIONS

Auricchio, Angelo , et al., "Dynamically Optimized Multi-site Resynchronizer", *U.S. Appl. No. 10/071,875, Filed Feb. 8, 2002.*

Brunner, Friedrich, et al., "Attenuation of myocardial ischemia/reperfusion injury in mice with myocyte-specific overexpression of endothelial nitric oxide synthase", *Cardiovascular Research, 57,* (2003),55-62.

Ferdinandy, Peter , et al., "Nitric oxide, superoxide, and peroxynitrite in myocardial ischaemia-reperfusion injury and preconditioning", *British Journal of Pharmacology, vol. 138, No. 4,* (2003),532-543.

Braunwald, et al., "Sustained Paired Electrical Stimuli; Slowing of the Ventricular Rate and Augmentation of Contractile Force", *American Journal of Cardiology, 14,* (1964),pp. 285 & 385-393.

Hada, Yoshiyuki , et al., "Pulsus alternans determined by biventricular simultaneous systolic time intervals", *Circulation, vol. 65, No. 3,* (Mar. 1982),617-26.

Konta, Tsuyoshi , et al., "Significance of Discordant ST Alternans in Ventricular Fibrillation", *Circulation, vol. 82, No. 6, Dec. 1990,* American Heart Association,(1990),2185-2189.

Lee, Y. C. , et al., "Pulsus alternans in patients with congestive cardiomyopathy", *Circulation, vol. 65, No. 7,* (Jun. 1982),1533-4.

Rubenstein, Donald S., et al., "Premature Beats Elicit a Phase Reversal of Mechanoelectrical Alternans in Cat Ventricular Myocytes", *Circulation, vol. 91, No. 1, Jan. 1995,* American Heart Association,(Jan. 1, 1995),201-214.

Sabbah, et al., "Delivery of Non-Excitatory Contractility-Modulation Electric Signals Improve Left Ventricular Performance in Dogs with Heart Failure", *Circulation, Supplement 1, 100 (18),* Abstract No. 631,(Nov. 2, 1999),pp. 1-122.

Schaefer, S , et al., "Clinical and hemodynamic characteristics of patients with inducible pulsus alternans", *American Heart Journal, vol. 115, No. 6,* (Jun. 1988),1251-7.

Smith, Damon , et al., "Influence of the Aortic Component of the Second Heart Sound on Left Ventricular Maximal Negative dP/dt in the Dog", *American Journal of Cardiology, 55: 205,* (1985),205-209.

Watanabe, Michiko , et al., "Developmental Remodeling and Shortening of Cardiac Outflow Tract Involves Myocyte Programmed Cell Death", *Development, 125 (19),* (1998), 3809-3820.

vol. 98, No. 2, (Jan. 16, 2001),735-740.

Gewaltig, Michael T., et al., "Vasoprotection ny nitric oxide: mechanisms and therapeutic potential", *Cardiovascular Research, 55,* (Feb. 14, 2002),250-260.

Li, Qianghong , et al., "Gene Therapy With Inducible Nitric Oxide Synthase Protects Against Myocardial Infarction via a Cyclooxygenase-2-Dependent Mechanism", *Circulation Research, 92,* (2003),741-748.

Ostadal, Petr , et al., "The effect of early treatment by cerivastatin on the serum level of C-reactive protein, interleukin-6, and interleukin-8 in patients with unstable angina and non-Q-wave myocardial infarction", *Molecular and Cellular Biochemistry, 246,* (2003),45-50.

Paolocci, Nazareno , et al., "Positive inotropic and lusitropic effects of HNO/NO- in failing hearts: Independence from beta-adrenergic signaling", *PNAS, vol. 100, No. 9,* (Apr. 29, 2003),5537-5542.

Pastore, Joseph M., et al., "Method And Apparatus For Detecting Acoustic Oscillations In Cardiac Rhythm", *U.S. Appl. No. 10/138,046, Filed May 3, 2002,*, 25 pages.

Pastore, Joseph M., et al., "Method And Apparatus For Detecting Oscillations In Cardiac Rhythm", *U.S. Appl. No. 10/172,825, Filed Jun. 14, 2002,* 33 pages.

Salloum, Fadi, et al., "Sildenafil Induces Delayed Preconditioning Through Inducible Nitric Oxide Synthase-Dependent Pathway in Mouse Heart", *Circulation Research, 92,* (Apr. 4, 2003),595-597.

Suematsu, Yoshihiro, et al., "L-Arginine given after ischaemic preconditioning can enhance cardioprotection in isolated rat hearts", *European Journal of Cardio-thoracic Surgery, 19,* (2001),873-879.

Woldbaek, Per R., et al., "Increased cardiac IL-18 mRNA, pro-IL-18 and plasma IL-18 after myocardial infarction in the mouse; a potential role in cardiac dysfunction", *Cardiovascular Research, 59,* (2003),122-131.

Wolfrum, Sebastian, et al., "Acute Reduction of Myocardial Infarct Size By a Hydroxymethyl Glutaryl Coenzyme A Reductase Inhibitor Is Mediated By Endothelial Nitric Oxide Synthase", *J. Cardiovas Pharmacol, vol. 41, No. 3,* (Mar. 2003),474-480.

Wunderlich, Carsten, et al., "Acute Inhibition of Myoglobin Impairs Contractility and Energy State of iNOS-Overexpressing Hearts", *Circulation Research, 92,* (2003), 1352-1358.

Reiter, Michael J., et al., "Electrophysiological Effects of Acute Dilatation in the Isolated Rabbit Hear", *Circulation, vol. 96, No. 11,* (Dec. 2, 1997),4050-4056.

Yu, Yinghong, et al., "Dynamic Device Therapy Control For Treating Post Myocardial Infarction Patients", *U.S. Appl. No. 10/744,900, Filed Dec. 22, 2003,* 37 pgs.

\* cited by examiner

METHOD AND APPARATUS FOR ASSESSING AND TREATING MYOCARDIAL WALL STRESS

FIELD OF THE INVENTION

This invention pertains to apparatus and methods for the diagnosis and treatment of heart disease and to devices providing electrostimulation to the heart such as cardiac pacemakers.

BACKGROUND

Congestive heart failure (CHF) is a clinical syndrome in which an abnormality of cardiac function causes cardiac output to fall below a level adequate to meet the metabolic demand of peripheral tissues. CHF can be due to a variety of etiologies with that due to ischemic heart disease being the most common. Inadequate pumping of blood into the arterial system by the heart is sometimes referred to as "forward failure," with "backward failure" referring to the resulting elevated pressures in the lungs and systemic veins which lead to congestion. Backward failure is the natural consequence of forward failure as blood in the pulmonary and venous systems fails to be pumped out. Forward failure can be caused by impaired contractility of the ventricles due, for example, to coronary artery disease, or by an increased afterload (i.e., the forces resisting ejection of blood) due to, for example, systemic hypertension or valvular dysfunction. One physiological compensatory mechanism that acts to increase cardiac output is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism but at the expense of possible pulmonary and/or systemic congestion.

When the ventricles are stretched due to the increased preload over a period of time, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium which leads to alterations in cellular structure, a process referred to as ventricular remodeling. Hypertrophy can increase systolic pressures but also decreases the compliance of the ventricles and hence increases diastolic filling pressure to result in even more congestion. It also has been shown that the sustained stresses causing hypertrophy may induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the process ultimately results in both systolic and diastolic dysfunction. It has been shown that the extent of ventricular remodeling is positively correlated with increased mortality in CHF patients.

SUMMARY OF THE INVENTION

Disparate stresses in different areas of the heart are responsible for the undesirable remodeling discussed above. The present invention relates to an apparatus and method for acutely assessing myocardial wall stress at a local site by measuring the action potential duration at the site during systole, referred to herein as an activation-recovery interval. The invention may be incorporated into a cardiac rhythm management device having the capability of pacing and sensing multiple cardiac sites. Such a device may be programmed to measure activation-recovery intervals at one or more myocardial sites and identify stressed sites with a threshold criterion. The assessment of localized wall stress may then be used by a clinician in planning subsequent therapy. The device can also be programmed to deliver pacing pulses in a manner such that the stressed site or sites so identified are pre-excited relative to other myocardial regions during systole. Such pre-excitation serves to mechanically unload the stressed site and hence prevent or reverse myocardial remodeling.

DETAILED DESCRIPTION

Some form of cardiac pacing can often benefit CHF patients. For example, sinus node dysfunction resulting in bradycardia can contribute to heart failure which can be corrected with conventional bradycardia pacing. Also, some CHF patients suffer from some degree of AV block such that their cardiac output is improved by synchronizing atrial and ventricular contractions with dual-chamber pacing using a programmed AV delay time (i.e., atrial triggered ventricular pacing or AV sequential pacing). CHF patients may also suffer from conduction defects of the specialized conduction system of the heart (a.k.a. bundle branch blocks) so that a depolarization impulse from the AV node reaches one ventricle before the other. Stretching of the ventricular wall brought about by CHF can also cause slowed conduction of depolarization impulses through the ventricle. If conduction velocity is slowed in the left ventricle more than the right, for example, the contraction of the two ventricles during ventricular systole becomes uncoordinated which lessens pumping efficiency. The contraction of a single ventricle may also become uncoordinated due to intraventricular conduction defects. In these situations, cardiac output can be increased by improving the synchronization of right and left ventricular contractions with cardiac resynchronization pacing.

In multi-site resynchronization pacing, the atria or ventricles are paced at more than one site in order to affect a spread of excitation that results in a more coordinated contraction. Biventricular pacing is one example of multi-site pacing in which both ventricles are paced in order to synchronize their respective contractions. Multi-site pacing may also be applied to only one chamber. For example, a ventricle may be paced at multiple sites with pacing pulses in order to produce multiple waves of depolarization that emanate from the pacing sites. This may produce a more coordinated contraction of the ventricle and thereby compensate for intraventricular conduction defects that may exist.

Altering the coordination of ventricular contractions with multi-site pacing can also be used to deliberately change the distribution of wall stress experienced by the ventricle during the cardiac pumping cycle. The degree to which a heart muscle fiber is stretched before it contracts is termed the preload. The maximum tension and velocity of shortening of a muscle fiber increases with increasing preload. The increase in contractile response of the heart with increasing preload is known as the Frank-Starling principle. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region that contracts later than other regions is subjected to both an increased preload and afterload. This situation is created frequently by the ventricular conduction delays associated with heart failure and ventricular dysfunction.

The heart's initial physiological response to the uneven stress resulting from an increased preload and afterload is compensatory hypertrophy in those later contracting regions of the myocardium. In the later stages of remodeling, the regions may undergo atrophic changes with wall thinning due to the increased stress. The parts of the myocardium that contract earlier in the cycle, on the other hand, are subjected to less stress and are less likely to undergo hypertrophic remodeling. The present invention makes use of this phenomena in order to effect reversal of remodeling by pacing one or more sites in a ventricle (or an atrium) with one or more excitatory stimulation pulses during a cardiac cycle with a specified pulse output sequence. The pace or paces are delivered in a manner that excites a previously stressed and remodeled region of the myocardium earlier during systole so that it experiences less afterload and preload. This pre-excitation of the remodeled region relative to other regions unloads the region from mechanical stress and allows reversal of remodeling to occur.

In another application of the invention, pre-excitation stimulation may be used to unload a stressed myocardial region that has been weakened by ischemia or other causes. Such regions of the myocardium may be particularly vulnerable to dilation and formation of aneurysms. An increased preload and afterload also requires an increased energy expenditure by the muscle which, in turn, increases its perfusion requirements and may result in further ischemia. Pre-excitation of an ischemic region may thus reduce the region's need for blood as well as reduce the mechanical stress to which the region is subjected during systole to reduce the likelihood of further dilation.

As detailed below, the present invention provides a means by which a pacemaker capable of multi-site sensing and pacing may identify stressed sites. The device may then be programmed to alter its pacing operation in a manner that reduces the stress to those sites.

1. Hardware Platform

Cardiac rhythm management devices such as pacemakers are usually implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
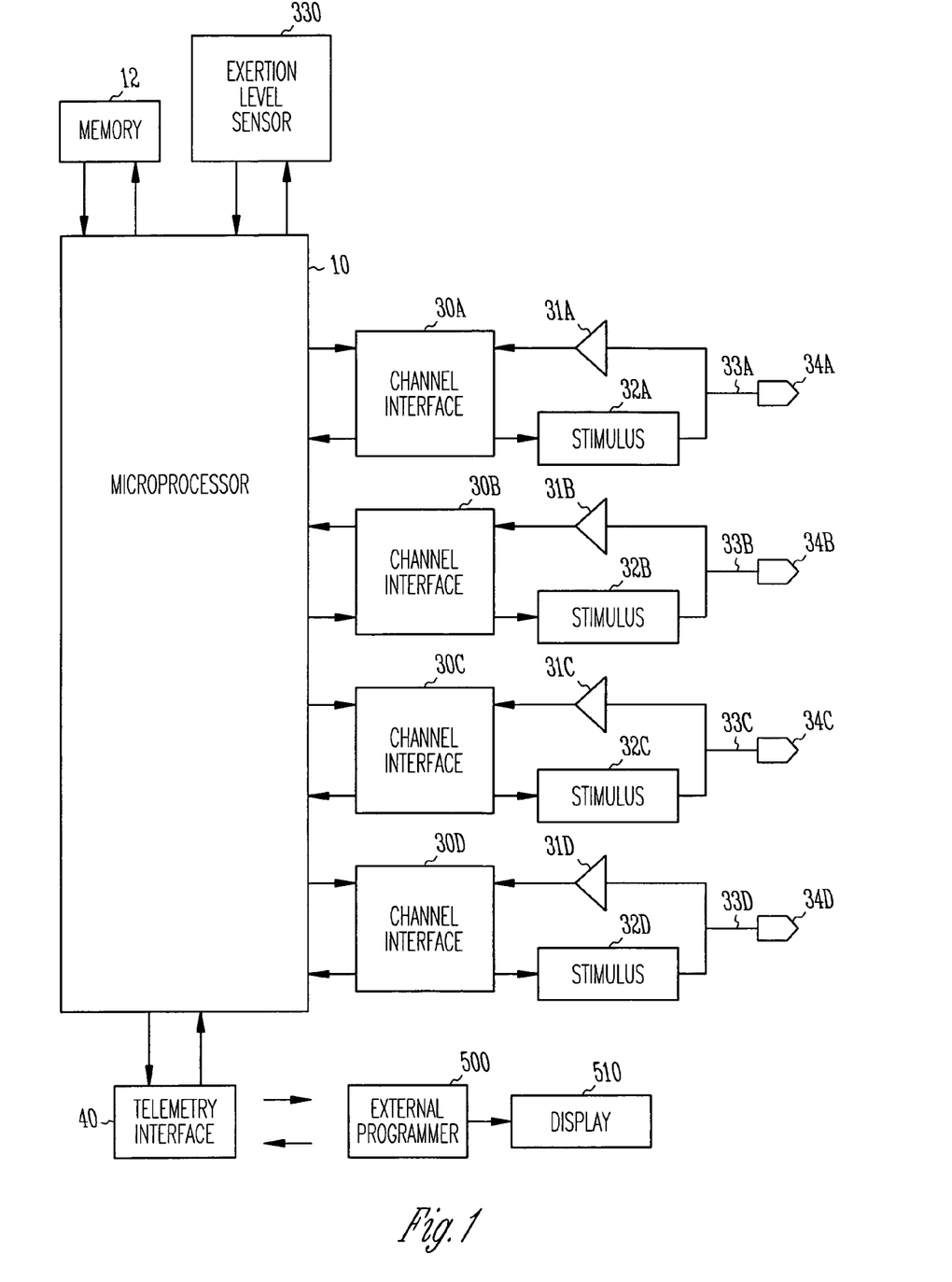
FIG. 1 is a block diagram of an exemplary cardiac rhythm management device for practicing one embodiment of the present invention.

FIG. 1 shows a system diagram of a microprocessor-based pacemaker equipped with multiple sensing and pacing channels which may be physically configured to sense and/or pace multiple sites in the atria or the ventricles. The controller 10 of the pacemaker is a microprocessor which communicates with a memory 12 via a bidirectional data bus. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. The memory 12 typically comprises a ROM (read-only memory) for program storage and a RAM (random-access memory) for data storage. Shown in the figure are four exemplary sensing and pacing channels designated "a" through "d" comprising electrodes 34*a–d*, leads 33*a–d*, sensing amplifiers 31*a–d*, pulse generators 32*a–d*, and channel interfaces 30*a–d* which. Although only one electrode for each lead is shown in the figure, the leads may be either unipolar leads, where a single electrode referenced to the device housing is used for sensing and pacing, or bipolar leads which include two closely spaced electrodes for sensing and pacing. The channel interfaces 30*a–d* communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. An exertion level sensor 330 (e.g., an accelerometer, a minute ventilation sensor, or other sensor that measures a parameter related to metabolic demand) enables the controller to adapt the pacing rate in accordance with changes in the patient's physical activity. A telemetry interface 40 is also provided for communicating with an external programmer 500 which has an associated display 510.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. Multiple excitatory stimulation pulses can also be delivered to multiple sites during a cardiac cycle in order to both pace the heart in accordance with a bradycardia mode and provide resynchronization of contractions to compensate for conduction defects.

The device shown in FIG. 1 can be configured such that multiple cardiac sites are sensed and/or paced. As described below, this allows those sites to be monitored to determine if any are experiencing increased wall stress. Once one or more such sites are identified, the device may be programmed to initiate stress reduction pacing that pre-excites the stressed site or sites. Initiation of stress reduction pacing may involve altering the device's pulse output configuration and/or sequence, where the pulse output configuration specifies a specific subset of the available electrodes to be used for delivering pacing pulses and the pulse output sequence specifies the timing relations between the pulses.

2. Assessment of Myocardial Wall Stress

Figure 2:
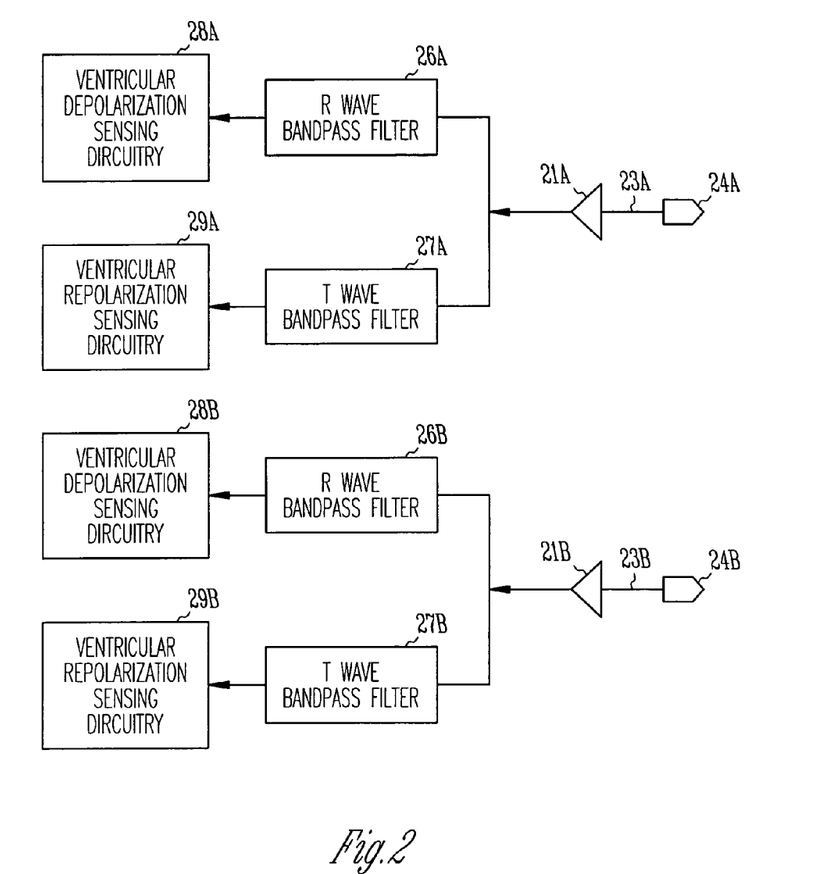
FIG. 2 is a block diagram of sensing channel components for detecting ventricular depolarizations and repolarizations.

In order to assess local myocardial wall stress, the action potential duration during systole, also referred to herein as the activation-recovery interval, can be measured by a device such as shown in FIG. 1 at those sites where sensing electrodes are disposed. Because the bipolar electrodes "see" a smaller volume of the myocardium, it may be desirable to use bipolar sensing electrodes rather than unipolar electrodes for measuring the activation-recovery interval at the electrode sites. In one implementation, the controller is programmed to measure the activation-recovery interval as the time between a detected depolarization and a detected repolarization in an electrogram generated by a sensing channel. Sensing channels can be designed to detect both depolarizations (i.e., conventional atrial or ventricular senses) and repolarizations. FIG. 2 illustrates how this may be implemented in a ventricular sensing channel. When the channel is awaiting a ventricular sense, the electrogram signal is passed through an R wave bandpass filter (26a or 26b) with passband characteristics selected to match the frequency content of a ventricular depolarization. The ventricular depolarization sensing circuitry (28a or 28b) then compares the filtered electrogram signal with a threshold to detect when a ventricular sense occurs. After a ventricular sense occurs, the channel awaits a ventricular repolarization during a specified time frame (e.g., between 50 and 500 milliseconds after the ventricular depolarization). During this time, the electrogram signal is passed through a T wave bandpass filter (27a or 27b) that has a passband characteristic conforming to the frequency content of a ventricular repolarization which is generally lower than that of a ventricular depolarization. The ventricular repolarization sensing circuitry (29a or 29b) then compares the filtered electrogram signal with a threshold to determine when the repolarization occurs. The channel may continue to monitor for depolarizations during this time in case the repolarization is undersensed. A similar scheme with atrial depolarization and repolarization bandpass filters and sensing circuits may be implemented to detect atrial repolarizations.

The bandpass filters in FIG. 1B may be implemented as analog filters that operate directly on the electrogram signal received from the electrodes or may be switched capacitor-type filters that sample the electrogram signal into a discrete-time signal which is then filtered. Alternatively, the electrogram signal can be sampled and digitized by an A/D converter in the channel interface with the bandpass filtering implemented in the digital domain by a dedicated processor or code executed by the controller 10.

After measuring the activation-recovery interval at a plurality of myocardial sites, sites that are stressed may be identified with a specified threshold criterion applied to the activation-recovery interval. That is, a site is identified as stressed when its measured activation-recovery interval is below the specified threshold value. Because the cardiac action potential normally varies with heart rate, it may be desirable to measure activation-recovery intervals during intrinsic beats for the purpose of assessing myocardial stress only when the heart rate is within a specified range. Activation-recovery intervals can also be measured during paced beats while pacing pulses are delivered at a specified rate. In the case of a paced beat, the depolarization corresponds to an evoked response detected by the sensing channel, while the repolarization is similar to an intrinsic beat. Alternatively, the threshold criterion for assessing myocardial wall stress based upon the activation-recovery interval may be adjusted in accordance with the measured intrinsic heart rate or pacing rate.

Another technique that can be used to identify stressed sites is the phenomena of mechanical alternans. When oscillations in pulse pressure are detected in a patient, referred to as pulsus alternans it is generally interpreted by clinicians as a sign of left ventricular dysfunction. Localized alternations in local wall stress, as revealed by alternations in the activation-recovery interval, may similarly indicate that the site is subjected to increased stress. Stressed sites may therefore be identified by detecting oscillations in the measured activation-recovery interval either instead of, or in addition to, the threshold criterion for the activation-recovery interval discussed above.

Once one or more stressed sites are identified, the information may be communicated to an external programmer via a telemetry link and used by a clinician in planning further treatment. A wall stress parameter for each electrode site may be determined from the length of the activation-recovery interval as well as a parameter representing the average overall myocardial wall stress. As described below, the device may also be programmed to alter its pacing mode so as to mechanically unload one or more of the stressed sites.

3. Pacing to Unload Stressed Sites

One or more myocardial pacing sites identified as stressed may be mechanically unloaded during systole by delivering one or more pacing pulses in a manner such that the stressed site or sites are pre-excited relative to other regions of the myocardium. Such pacing subjects the stressed sites to a lessened preload and afterload during systole, thus reducing the wall stress. By unloading a myocardial region in this way over a period of time, reversal of undesirable myocardial remodeling may also be effected. Pre-excitation may also be applied to stressed regions of the myocardium that have been weakened by ischemia or other causes in order to prevent further dilation and/or promote healing.

Pacing for myocardial wall stress reduction may be delivered in accordance with a programmed bradycardia pacing mode and thus also provide therapy for bradycardia as well. Such pacing also may or may not include multi-site pacing for purpose of also providing cardiac resynchronization therapy. What effects localized stress reduction is the pre-excitation of one or more myocardial regions relative to other regions during systole. This may be accomplished in certain situations with single-site pacing and in others with multi-site resynchronization pacing that also improves the pumping function of the heart. In the latter case, the pacing pulse output configuration and sequence that produces optimum resynchronization may or may not also deliver optimum therapy for reduction of myocardial wall stress.

In an exemplary embodiment, a device such as illustrated in FIG. 1A is configured with a plurality of pacing/sensing electrodes disposed in both ventricles at selected sites. The device is programmed to normally deliver pacing pulses to selected ones of the available pacing electrodes, referred to as a pulse output configuration, and in a specified time sequence, referred to as a pulse output sequence. One such site then is identified as a stressed site by measurement of activation-recovery intervals at the electrodes during either intrinsic or paced beats, and the device is programmed by initiate stress reduction pacing for that site. In one example, the device normally delivers bradycardia pacing at a single ventricular site, and then switches the pacing configuration to deliver pacing pulses to the stressed site. Single-site pacing that pre-excites the ventricle at this site results in the stressed site being excited before other regions of the ventricular myocardium as the wave of excitation spreads from the paced site. In another example, the device is programmed to deliver resynchronization pacing with multiple paces delivered to one or both ventricles during a cardiac cycle. In order to reduce stress at the identified site, the pulse output configuration is modified, if necessary, to include the stressed site, and the pulse output sequence is selected such that the stressed site is excited before other regions as the wave of excitation spreads from the multiple pacing sites.

Figure 3:
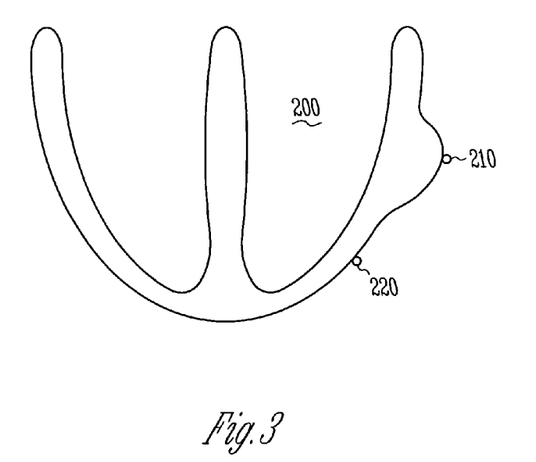
FIG. 3 depicts an exemplary placement of sensing/pacing electrodes in the left ventricle.

A more specific example is illustrated with reference to FIG. 3 which depicts a left ventricle 200 with sites 210 and 220 to which are fixed epicardial pacing/sensing electrodes. The device of FIG. 1 delivers pacing pulses to one or both sites in accordance with a biventricular or left ventricle-only pacing mode through its pacing channels. The myocardium at pacing site 210 is shown as being hypertrophied as compared to the myocardium at pacing site 220, presumably due to increased wall stress at site 210. The device then identifies the site 210 as a stressed site and initiates stress reduction pacing. In order to unload the hypertrophied site 210 during systole and thereby promote reversal of the hypertrophy, the device delivers pacing with a pulse output sequence that stimulates the hypertrophied site 210 before the other site 220. The lessened mechanical stress during systole then allows the site 210 to undergo reversal of the hypertrophy. In another example, both the right and left ventricles are paced at separate sites by pacing pulses delivered with a specified biventricular delay between the pulses delivered to each ventricle. If one of the pacing sites is identified as a stressed site, the biventricular delay can be adjusted so that the stressed ventricular pacing site is pre-excited relative to the other to change the wall stresses developed near these sites during systolic contraction.

In addition to pre-exciting selected sites in order to prevent or promote reversal of myocardial remodeling, such pre-excitation may also reduce the average wall stress of the heart and, consequently, its total workload. Such an effect may be desirable when the heart's blood supply is compromised due to coronary disease. As noted above, measurement of activation-recovery intervals at a plurality of sites can be used to compute an average wall stress parameter. The device may therefore be programmed to try different pacing output sequences and/or configurations, compute the average wall stress parameter for each, and then select the pulse output sequence and configuration that minimizes the parameter.

In the examples described above, the device is programmed to alter its pacing mode when a stressed site is identified by modifying the pulse output configuration and/or sequence to pre-excite the stressed site. Stress reduction pacing may be augmented where the pacing pulses are delivered in a demand mode by decreasing the escape interval used to pace the stressed site (e.g., the ventricular escape interval or the AV delay interval in the case of dual-chamber pacing). In another example, the device is configured with multiple sensing/pacing electrodes but is programmed to deliver neither bradycardia nor resynchronization pacing during normal operation. After a stressed site is identified, a pacing mode is initiated such that the stressed site is pre-excited in a timed relation to a triggering event that indicates an intrinsic beat has either occurred or is imminent such as immediately following the earliest detection of intrinsic activation elsewhere in the ventricle. Such activation may be detected from an electrogram with a conventional ventricular sensing electrode. An earlier occurring trigger event may be detected by extracting the His bundle conduction potential from a special ventricular sensing electrode using signal processing techniques.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac rhythm management device, comprising:
sensing channels for sensing cardiac electrical activity at a plurality of myocardial sites;
pacing channels for delivering pacing pulses to one or more myocardial sites;
a controller for controlling the delivery of pacing pulses in accordance with a programmed pacing mode;
circuitry for measuring activation-recovery intervals at a plurality of myocardial sites indicative of myocardial wall stress; and,
circuitry for identifying one or more stressed myocardial sites based upon the measured activation-recovery intervals.

2. The device of claim 1 further comprising circuitry for delivering pacing pulses in a selected pulse output sequence such that an identified stressed site is excited before other myocardial regions during systole.

3. The device of claim 1 further comprising circuitry for switching a pulse output configuration that defines which pacing channels are used during a cardiac cycle such that an identified stressed site is excited before other myocardial regions during systole.

4. The device of claim 1 further comprising circuitry for measuring an activation-recovery interval as the time between a detected depolarization and a detected repolarization in an electrogram generated by a sensing channel.

5. The device of claim 1 further comprising circuitry for measuring activation-recovery intervals in order to identify stressed sites during intrinsic beats when a measured heart rate is within a specified range.

6. The device of claim 1 further comprising circuitry for measuring activation-recovery intervals in order to identify stressed sites during paced beats while delivering pacing pulses at a specified rate.

7. The device of claim 1 further comprising circuitry for adjusting a criterion for identifying stressed sites based upon measured activation-recovery intervals in accordance with measured heart rate.

8. The device of claim 1 further comprising circuitry for computing an average myocardial wall stress parameter based upon activation-recovery intervals measured at a plurality of myocardial sites.

9. The device of claim 8 wherein further comprising circuitry for delivering pacing pulses with a pulse output configuration and in a pulse output sequence selected to pre-excite particular myocardial sites and reduce the average myocardial wall stress.

10. The device of claim 1 further comprising circuitry for measuring activation-recovery intervals and identify stressed myocardial sites at periodic time intervals.

11. The device of claim 1 wherein the sensing and pacing channels are configured to pace and sense ventricular sites further comprising:
    circuitry for delivering pacing pulses to one or more ventricular sites in accordance with a programmed pacing mode; and
    circuitry for switching a pulse output configuration and a pulse output sequence defining the pacing mode in order to pre-excite identified stressed ventricular sites.

12. A method for operating a cardiac rhythm management device, comprising:
    sensing cardiac electrical activity at a plurality of myocardial sites;
    delivering pacing pulses to one or more myocardial sites;
    measuring activation-recovery intervals at a plurality of myocardial sites indicative of myocardial wall stress; and,
    identifying one or more stressed myocardial sites based upon the measured activation-recovery intervals.

13. The method of claim 12 further comprising delivering pacing pulses in a selected pulse output sequence such that an identified stressed site is excited before other myocardial regions during systole.

14. The method of claim 12 further comprising switching a pulse output configuration that defines which pacing channels are used during a cardiac cycle such that an identified stressed site is excited before other myocardial regions during systole.

15. The method of claim 12 further comprising measuring an activation-recovery interval as the time between a detected depolarization and a detected repolarization in an electrogram.

16. The method of claim 12 further comprising measuring activation-recovery intervals in order to identify stressed sites during intrinsic beats when a measured heart rate is within a specified range.

17. The method of claim 12 further comprising measuring activation-recovery intervals in order to identify stressed sites during paced beats while delivering pacing pulses at a specified rate.

18. The method of claim 12 further comprising adjusting a criterion for identifying stressed sites based upon measured activation-recovery intervals in accordance with measured heart rate.

19. The method of claim 12 further comprising computing an average myocardial wall stress parameter based upon activation-recovery intervals measured at a plurality of myocardial sites.

20. The method of claim 19 further comprising delivering pacing pulses with a pulse output configuration and in a pulse output sequence selected to pre-excite particular myocardial sites and reduce the average myocardial wall stress.

21. The method of claim 12 further comprising identifying stressed sites with a threshold criterion applied to the measured activation-recovery intervals.

22. The method of claim 12 further comprising identifying a stressed site when an oscillation is detected in the measured activation-recovery interval at that site.

* * * * *